(12) United States Patent
Takagi

(10) Patent No.: US 10,285,630 B2
(45) Date of Patent: May 14, 2019

(54) BIOLOGICAL INFORMATION MEASUREMENT SYSTEM AND BIOLOGICAL INFORMATION MEASUREMENT METHOD

(71) Applicant: Trilobite Co., Ltd., Tokyo (JP)

(72) Inventor: Ruita Takagi, Tokyo (JP)

(73) Assignee: Trilobite Co. Ltd. (JP)

( * ) Notice: Subject to any disclaimer, the term of this patent is extended or adjusted under 35 U.S.C. 154(b) by 0 days.

(21) Appl. No.: 15/554,474

(22) PCT Filed: Apr. 28, 2017

(86) PCT No.: PCT/JP2017/017001
§ 371 (c)(1),
(2) Date: Aug. 30, 2017

(87) PCT Pub. No.: WO2017/191816
PCT Pub. Date: Nov. 9, 2017

(65) Prior Publication Data
US 2018/0160948 A1 Jun. 14, 2018

(30) Foreign Application Priority Data
May 2, 2016 (JP) ................................ 2016-092726

(51) Int. Cl.
*A61B 5/1455* (2006.01)
*A61B 5/026* (2006.01)
(Continued)

(52) U.S. Cl.
CPC ............ *A61B 5/1455* (2013.01); *A61B 5/002* (2013.01); *A61B 5/026* (2013.01);
(Continued)

(58) Field of Classification Search
CPC .............. A61B 5/14551; A61B 5/1455; A61B 5/14553; A61B 5/0059; A61B 5/0075
See application file for complete search history.

(56) References Cited

U.S. PATENT DOCUMENTS 7,190,999 B2 * 3/2007 Geheb ...................... A61B 5/11
600/515
7,569,018 B1 8/2009 Geddes et al.
(Continued)

FOREIGN PATENT DOCUMENTS

JP 09-140715 A 6/1997
JP 2008-173140 7/2008
(Continued)

OTHER PUBLICATIONS

Office Action dated Oct. 24, 2016 in corresponding Japanese Application No. 2016-092726 with English translation.
(Continued)

*Primary Examiner* — Eric F Winakur
(74) *Attorney, Agent, or Firm* — DLA Piper LLP (US)

(57) ABSTRACT

A biological information measurement system includes a light emitting portion, a light receiving portion, a light detection portion, a wireless transmission portion, a reception portion that receives information to specify a change corresponding to an increase or a decrease in the concentration or the amount of hemoglobin, wirelessly transmitted from the wireless transmission portion, and a determination portion that monitors information regarding a change in a blood flow based on the information for specifying a change corresponding to an increase or a decrease in the concentration or the amount of hemoglobin, received by the reception portion, over time, and determines whether or not a rate of the change in a blood flow exceeds a predetermined reference value in a case where there is a change in the
(Continued)

information regarding a change in a blood flow according to a timing of chest compressions of the subject.

15 Claims, 9 Drawing Sheets

(51) Int. Cl.
  *A61B 5/00* (2006.01)
  *A61B 5/024* (2006.01)
  *A61H 31/00* (2006.01)

(52) U.S. Cl.
  CPC ........ *A61B 5/02416* (2013.01); *A61B 5/6814* (2013.01); *A61H 31/004* (2013.01)

(56) References Cited

U.S. PATENT DOCUMENTS

| | | | |
|---|---|---|---|
| 2008/0171311 A1* | 7/2008 | Centen | A61H 31/005 434/265 |
| 2008/0259337 A1 | 10/2008 | Sagara et al. | |
| 2012/0245442 A1 | 9/2012 | Ukawa | |
| 2014/0058233 A1* | 2/2014 | Koyama | A61B 5/1455 600/322 |
| 2014/0275888 A1 | 9/2014 | Wegerich et al. | |
| 2015/0025344 A1* | 1/2015 | Benni | A61B 5/14552 600/323 |
| 2015/0051464 A1 | 2/2015 | Ozaki et al. | |
| 2015/0105636 A1* | 4/2015 | Hayman | A61B 5/14552 600/324 |
| 2018/0110449 A1* | 4/2018 | Maeda | A61B 5/14552 |

FOREIGN PATENT DOCUMENTS

| | | |
|---|---|---|
| JP | 2009-101057 A | 5/2009 |
| JP | 2013-170881 | 9/2013 |
| JP | 2014-064929 A | 4/2014 |

OTHER PUBLICATIONS

Office Action dated Feb. 1, 2017 in corresponding Japanese Application No. 2016-092726 with English translation.

Office Action dated Apr. 17, 2017 in corresponding Japanese Application No. 2016-092726 with English translation.

Supplementary European Search Report dated Jun. 5, 2018, from counterpart European Application No. 17754591.0.

Office Action dated Feb. 6, 2019, of counterpart European Application No. 17754591.0.

* cited by examiner

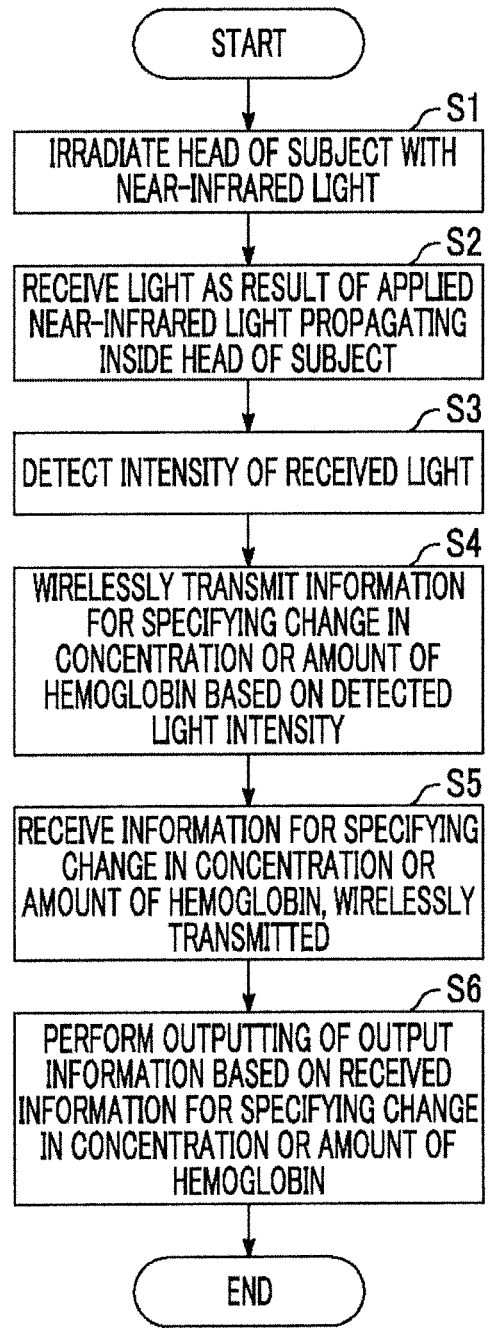

BIOLOGICAL INFORMATION MEASUREMENT SYSTEM AND BIOLOGICAL INFORMATION MEASUREMENT METHOD

TECHNICAL FIELD

This disclosure relates to a biological information measurement system including a biological information measurement section and a biological information output section, and a biological information measurement method.

BACKGROUND

In a medical field of the related art, a communication cable (wire) that transmits information measured by a measurement apparatus to an output apparatus is present between the measurement apparatus measuring biological information of a subject such as a patient and the output apparatus outputting the information measured by the measurement apparatus.

The presence of such a communication cable may impede action of a medical worker when the medical worker performs other medical practices while measuring biological information of a subject such as a patient with the measurement apparatus, and there is also concern that a medical accident may occur due to entangling of the communication cable.

On the other hand, a restriction is imposed on a subject such as a patient since the subject is required to maintain a posture thereof to be constant to some degree during measurement of biological information due to the presence of the communication cable, and thus a burden is placed on the subject such as a patient.

Due to the presence of the communication cable, there is a possibility that a signal of measurement information may be attenuated in the process of transmitting measurement information obtained by the measurement apparatus measuring biological information to the output apparatus, or the influence of disturbance is also pointed out when another communication system apparatus is used around the measurement apparatus measuring biological information.

For example, JP2014-64929A discloses that in which a pulse oxygen measurement sensor is attached to a patient, and a modulated red light and infrared photo-plethysmograph signal is transmitted to a universal/upgrading pulse oximeter (UPO) for patient monitoring through a patient cable, and discloses that the UPO computes the patient's oxygen saturation and pulse rate on the basis of the sensor signal and, optionally, displays the patient's oxygen status.

However, in the universal/upgrading pulse oximeter (UPO) for patient monitoring disclosed in JP2014-64929A, biological information of a patient is monitored without interruption, but a communication system cable is presented between a measurement apparatus measuring biological information and an output apparatus.

Therefore, in the UPO disclosed in JP2014-64929A, when a medical worker performs measurements of biological information on a subject such as a patient, the medical worker cannot smoothly perform such medical practice tasks, and a restriction is imposed on the posture of the subject such as a patient during measurement, and thus a burden may be placed on the subject such as a patient. It could therefore be helpful to provide a biological information measurement system and a biological information measurement method in which, when a medical worker performs measurement of biological information on a subject such as a patient, the medical worker can easily perform smooth medical practice, and a restriction imposed on a posture of the subject such as a patient during measurement can be alleviated.

SUMMARY

I thus provide a biological information measurement system applied to a subject requiring cardiopulmonary resuscitation, including a biological information measurement section; and a biological information output section, in which the biological information measurement section includes a light emitting portion that irradiates the head of the subject with near-infrared light, a light receiving portion that receives light as a result of the near-infrared light applied from the light emitting portion propagating inside the head of the subject, a light detection portion that detects the intensity of the light received by the light receiving portion, and a wireless transmission portion that wirelessly transmits information to specify a change corresponding to an increase or a decrease in the concentration or the amount of hemoglobin in blood based on the light intensity detected by the light detection portion, and in which the biological information output section includes a reception portion that receives the information to specify a change corresponding to an increase or a decrease in the concentration or the amount of hemoglobin, wirelessly transmitted from the wireless transmission portion of the biological information measurement section, and a determination portion that monitors information regarding a change in a blood flow based on the information for specifying a change corresponding to an increase or a decrease in the concentration or the amount of hemoglobin, received by the reception portion, over time, and determines whether or not a rate of the change in a blood flow exceeds a predetermined reference value when there is a change in the information regarding a change in a blood flow according to a timing of chest compressions of the subject.

Preferably, the light emitting portion of the biological information measurement section irradiates the head of the subject with near-infrared light having three different wavelengths, and the three different wavelengths are a first wavelength $\lambda_1$ (770 nm±20 nm), a second wavelength $\lambda_2$ (805 nm±20 nm), and a third wavelength $\lambda_3$ (870 nm±20 nm).

Preferably, the light emitting portion and the light receiving portion of the biological information measurement section include a light emitting portion (o1) and a light receiving portion (p1) for performing measurement, provided on the left as a pair, and a light emitting portion (o2) and a light receiving portion (p2) for performing measurement, provided on the right as a pair, and the order of eight times of irradiation performed every cycle by using near-infrared light having three different wavelengths is any one of the following orders of A→B→C→D→E→F→G→H, B→C→D→E→F→G→H→A, C→D→E→F→G→H→A→B, D→E→F→G→H→A→B→C→, E→F→G→H→A→B→C→D, F→G→H→A→B→C→D→E→, G→H→A→B→C→D→E→F, and H→A→B→C→D→E→F→G:

A: o1 (left) first wavelength $\lambda_1$ (770 nm±20 nm)
B: o1 (left) second wavelength $\lambda_2$ (805 nm±20 nm)
C: o1 (left) third wavelength $\lambda_3$ (870 nm±20 nm)
D: o2 (right) second wavelength $\lambda_2$ (805 nm±20 nm)
E: o2 (right) first wavelength $\lambda_1$ (770 nm±20 nm)

F: o1 (left) second wavelength $\lambda_2$ (805 nm±20 nm)
G: o2 (right) third wavelength $\lambda_3$ (870 nm±20 nm)
H: o2 (right) second wavelength $\lambda_2$ (805 nm±20 nm).

The orders of A: o1 (left) first wavelength $\lambda_1$ (770 nm±20 nm) and C: o1 (left) third wavelength $\lambda_3$ (870 nm±20 nm) may be replaced with each other, or the orders of E: o2 (right) first wavelength $\lambda_1$ (770 nm±20 nm) and G: o2 (right) third wavelength $\lambda_3$ (870 nm±20 nm) may be replaced with each other.

Preferably, when irradiation is performed eight times every cycle, irradiation from a first cycle to an eighth cycle is regarded as one set, one or more sets of irradiation is performed, and at least one set of irradiation is performed within one second.

The light emitting portion and the light receiving portion of the biological information measurement section may include a light emitting portion (o1) and a light receiving portion (p1) for performing measurement, provided on the left as a pair, and a light emitting portion (o2) and a light receiving portion (p2) for performing measurement, provided on the right as a pair, light beams having the three different wavelengths may be applied from the light emitting portions on of (left) and o2 (right) in the irradiation order, and the light detection portion may detect the intensities of light beams received by the light receiving portions on p1 (left) and p2 (right) in each cycle and, in respective pieces of data detected by the light detection portion in each cycle, when differences between pieces of data are all laid in the same direction (for example, all in an increase direction) through comparison between adjacent cycles, whereas differences between pieces of data are all laid in an opposite direction (for example, all in a decrease direction) through comparison between other adjacent cycles, the determination portion may determine that there is a change in a blood flow.

In the biological information measurement section, a light detection unit including the light emitting portion, the light receiving portion, and the light detection portion may have a first terminal, a wireless transmission unit including the wireless transmission portion may have a second terminal, and the first terminal and the second terminal may be directly connected to each other in an attachable and detachable manner.

In the biological information measurement section, a light detection unit including the light emitting portion, the light receiving portion, and the light detection portion may have a first terminal, a wireless transmission unit including the wireless transmission portion may have a second terminal, and the first terminal and the second terminal may be connected to each other via a wire.

The biological information measurement section may further include a display portion that displays display information based on the information to specify a change corresponding to an increase or a decrease in the concentration or the amount of hemoglobin, detected by the light detection portion.

The biological information output section may further include a display portion that displays display information based on the information to specify a change corresponding to an increase or a decrease in the concentration or the amount of hemoglobin, received by the reception portion.

The biological information measurement section may further include a calculation portion that performs a calculation process on the information to specify a change corresponding to an increase or a decrease in the concentration or the amount of hemoglobin, detected by the light detection portion.

The biological information output section may further include a calculation portion that performs a calculation process on the information to specify a change corresponding to an increase or a decrease in the concentration or the amount of hemoglobin, received by the reception portion.

When the determination portion determines that the predetermined reference value is exceeded, the biological information output section may perform outputting of output information based on notification information to notify the outside that the predetermined reference value is exceeded.

I also provide a biological information measurement method for a biological information measurement system applied to a subject requiring cardiopulmonary resuscitation, including a biological information measurement step executed in a biological information measurement section; and a biological information output step executed in a biological information output section, in which the biological information measurement step includes a light emission step of irradiating the head of the subject with near-infrared light, a light reception step of receiving light as a result of the near-infrared light applied in the light emission step propagating inside the head of the subject, a light detection step of detecting the intensity of the light received in the light reception step, and a wireless transmission step of wirelessly transmitting information to specify a change corresponding to an increase or a decrease in the concentration or the amount of hemoglobin in blood based on the light intensity detected in the light detection step, and in which the biological information output step includes a reception step of receiving the information to specify a change corresponding to an increase or a decrease in the concentration or the amount of hemoglobin, wirelessly transmitted in the wireless transmission step of the biological information measurement step, and a determination step of causing the biological information output section to monitor information regarding a change in a blood flow based on the information for specifying a change corresponding to an increase or a decrease in the concentration or the amount of hemoglobin, received in the reception step, over time, and determine whether or not a rate of the change in a blood flow exceeds a predetermined reference value when there is a change in the information regarding a change in a blood flow according to a timing of chest compressions of the subject.

It is possible to transmit measurement information obtained by a biological information measurement section to a biological information output section without using a communication system cable between the biological information measurement section and the biological information output section.

Therefore, it is possible to achieve an effect in which, when a medical worker performs measurement of biological information on a subject such as a patient, the medical worker can easily perform smooth medical practice, and a restriction imposed on a posture of the subject such as a patient during measurement can be alleviated.

BRIEF DESCRIPTION OF THE DRAWINGS

FIG. 9 is a flowchart illustrating an example of a process performed by the biological information measurement system 300 including the biological information measurement section 100 and the biological information output section 200.

DETAILED DESCRIPTION

With reference to FIGS. 1 to 9, examples will be described.

Summary of Biological Information Measurement System 300 including Biological Information Measurement Section 100 and Biological Information Output Section 200

Figure 1:
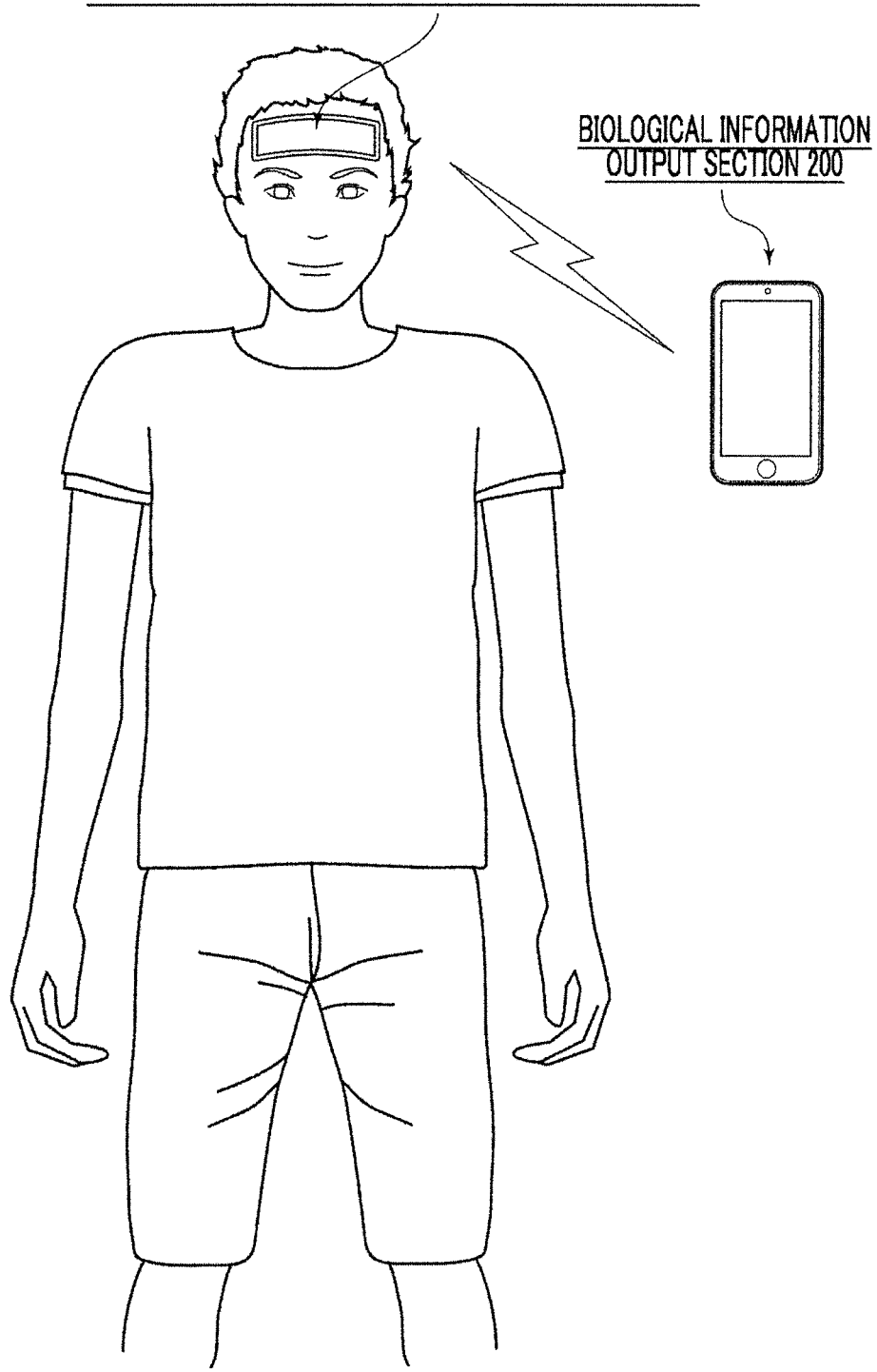
FIG. 1 is a diagram illustrating an example of an example of a biological information measurement system 300 in which measurement information obtained by a biological information measurement section 100 is wirelessly transmitted to a biological information output section 200 in a state in which the biological information measurement section 100 is attached (adhered) to the head of a subject such as a patient.

FIG. 1 is a diagram illustrating an example of a biological information measurement system 300 in which measurement information obtained by a biological information measurement section 100 is wirelessly transmitted to a biological information output section 200 in a state in which the biological information measurement section 100 is attached (adhered) to the head of a subject such as a patient.

The biological information measurement system 300 includes the biological information measurement section 100 and the biological information output section 200.

The biological information measurement section 100 includes a light emitting portion that irradiates the head of a subject with near-infrared light; a light receiving portion that receives light as a result of the near-infrared light applied from the light emitting portion propagating inside the head of the subject; a light detection portion that detects the intensity of the light received by the light receiving portion; and a wireless transmission portion that wirelessly transmits information to specify a change corresponding to an increase or a decrease in the concentration or the amount of hemoglobin in blood on the basis of the light intensity detected by the light detection portion.

On the other hand, the biological information output section 200 includes a reception portion that receives information to specify a change corresponding to an increase or a decrease in the concentration or the amount of hemoglobin, wirelessly transmitted from the wireless transmission portion of the biological information measurement section, and an output portion that outputs output information based on the information to specify a change corresponding to an increase or a decrease in the concentration or the amount of hemoglobin, received by the reception portion.

As illustrated in FIG. 1, the biological information measurement system 300 is realized by wirelessly transmitting measurement information obtained by the biological information measurement section 100 to the biological information output section 200 without using a communication cable between the biological information measurement section 100 and the biological information output section 200.

In the biological information measurement system 300, when a medical worker performs measurement of biological information on a subject such as a patient, the medical worker can perform smooth medical practice, and a restriction imposed on a posture of the subject such as a patient during measurement can be alleviated.

The biological information measurement section 100 of the biological information measurement system 300 measures the intensity of light as a result of near-infrared light applied to the head of a subject such as a patient propagating inside the head without being absorbed in the head, that is, the intensity (intensity of transmitted light) of light transmitted inside the head.

If blood flows (a blood flow changes) in a living body, it is known that the concentration or the amount of hemoglobin in blood changes. Conversely, if the concentration or the amount of hemoglobin in blood changes, it may be regarded that blood flows (a blood flow changes) in a living body.

I focus on the fact that, when the light emitting portion irradiates the head of a subject with near-infrared light, and the concentration or the amount of hemoglobin in blood increases, an amount (absorption amount) of the applied light in the near-infrared region absorbed in the head increases so that an amount (transmission amount) of the light in the near-infrared region transmitted inside the head is reduced, and an amount (reception amount) of light received by the light receiving portion is reduced due to the reduction in the transmission amount and, the fact that, when the concentration or the amount of hemoglobin in blood is reduced, an amount (absorption amount) of the applied light in the near-infrared region absorbed in the head is reduced so that an amount (transmission amount) of the light in the near-infrared region transmitted inside the head increases, and an amount (reception amount) of light received by the light receiving portion increases due to the increase in the transmission amount.

A configuration may be designed in which a current is output from the light receiving portion according to an amount (reception amount) of light received by the light receiving portion such as a photodiode (PD).

A flow of blood (a change in a blood flow) can be understood in real time by measuring the intensity (intensity of transmitted light) of light transmitted without being absorbed in the head by using the fact that an amount (transmission amount) of light in the near-infrared region transmitted inside the head differs depending on an increase or a decrease in the concentration or the amount of hemoglobin in blood of the head of a subject.

For example, when the biological information measurement system 300 is applied to a subject such as a patient requiring cardiopulmonary resuscitation, a medical worker can accurately adjust a position where cardiac massage (sternum pressing) is performed or massage force while checking a flow of blood (a change in a blood flow), and thus it is possible to improve a success probability of cardiopulmonary resuscitation.

Configuration of Biological Information Measurement System 300

Figure 2:
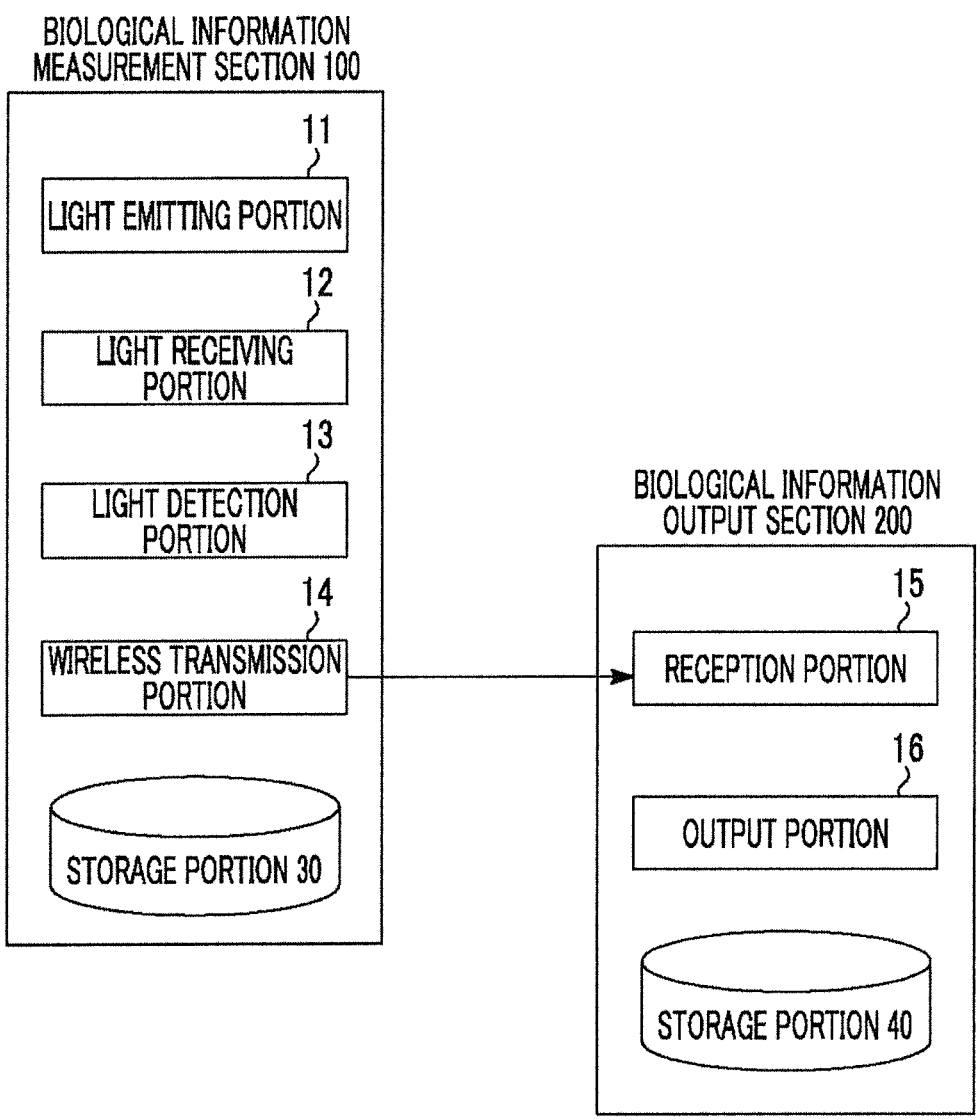
FIG. 2 is a block diagram illustrating examples of principal portion configurations of the biological information measurement section 100 and the biological information output section 200 forming the biological information measurement system 300.

FIG. 2 is a block diagram illustrating examples of principal portion configurations of the biological information measurement section 100 and the biological information output section 200 forming the biological information measurement system 300.

The biological information measurement system 300 includes the biological information measurement section 100 and the biological information output section 200 as exemplified in FIG. 1.

The biological information measurement section 100 includes a light emitting portion 11, a light receiving portion 12, a light detection portion 13, and a wireless transmission portion 14. The biological information measurement section 100 may further include a calculation portion and a display portion.

On the other hand, the biological information output section 200 includes a reception portion 15 and an output portion 16. The biological information output section 200 may further include a calculation portion, a display portion, and a determination portion.

Configuration of Biological Information Measurement Section 100 of Biological Information Measurement System 300

The light emitting portion 11 has a function of irradiating the head of a subject with near-infrared light. As the light emitting portion 11, for example, a light emitting diode (LED) may be used.

The light receiving portion 12 has a function of light as a result of the near-infrared light applied from the light emitting portion 11 propagating inside the head of the subject. As the light receiving portion 12, for example, a photodiode (PD) may be used.

The light detection portion 13 has a function of detecting the intensity of the light received by the light receiving portion 12. As the light detection portion 13, for example, a light detector that detects the intensity of light received by the light receiving portion 12, that is, the intensity (intensity of transmitted light) of light transmitted inside the head of a subject may be used.

The wireless transmission portion 14 has a function of wirelessly transmitting information to specify a change corresponding to an increase or a decrease in the concentration or the amount of hemoglobin in blood based on the light intensity detected by the light detection portion 13. For example, a device that can perform wireless transmission may be used as the wireless transmission portion 14, and a Bluetooth (registered trademark) method may be employed.

The "information for specifying a change corresponding to an increase or a decrease in the concentration or the amount of hemoglobin" may be information regarding a detection result of the light intensity (intensity of transmitted light) detected by the light detection portion 13, or may be information regarding a result obtained by converting the information regarding a detection result of the light intensity (intensity of transmitted light) detected by the light detection portion 13 into the concentration or the amount of hemoglobin.

As illustrated in FIG. 2, the biological information measurement section 100 may include not only the light emitting portion 11, the light receiving portion 12, the light detection portion 13, and the wireless transmission portion 14, described above, but also a calculation portion and a display portion (not illustrated) described below.

The calculation portion has a function of performing a calculation process on information for specifying a change corresponding to an increase or a decrease in the concentration or the amount of hemoglobin in blood based on the light intensity detected by the light detection portion 13. For example, the calculation portion performs a calculation process to convert information regarding a detection result of the light intensity (intensity of transmitted light) detected by the light detection portion 13 into information regarding the concentration or the amount of hemoglobin.

The display portion has a function of displaying display information based on the information to specify a change corresponding to an increase or a decrease in the concentration or the amount of hemoglobin in blood based on the light intensity detected by the light detection portion 13. For example, the display portion displays display information based on the information regarding a detection result of the light intensity (intensity of transmitted light) detected by the light detection portion 13 on a monitor or the like.

A storage portion 30 stores information acquired by each portion of the biological information measurement section 100. The storage portion 30 is formed of, for example, a nonvolatile semiconductor memory such as a flash memory.

Configuration of Biological Information Output Section 200 of Biological Information Measurement System 300

The reception portion 15 has a function of receiving information to specify a change corresponding to an increase or a decrease in the concentration or the amount of hemoglobin in blood based the light intensity, wirelessly transmitted from the wireless transmission portion 14 of the biological information measurement section 100. For example, a device that can perform wireless reception may be used as the reception portion 15, and a Bluetooth (registered trademark) method may be employed.

The output portion 16 has a function of outputting output information based on the information to specify a change corresponding to an increase or a decrease in the concentration or the amount of hemoglobin in blood based on the light intensity, received by the reception portion 15. The output portion 16 outputs the output information based on information regarding a detection result of the light intensity (intensity of transmitted light), received by the reception portion 15, to a monitor, a speaker, or the like.

As illustrated in FIG. 2, the biological information output section 200 may include not only the reception portion 15 and the output portion 16, described above, but also a calculation portion, a display portion, and a determination portion (not illustrated) described below.

The calculation portion has a function of performing a calculation process on information to specify a change corresponding to an increase or a decrease in the concentration or the amount of hemoglobin in blood based on the light intensity, received by the reception portion 15. For example, the calculation portion performs a calculation process to convert information regarding a detection result of the light intensity (intensity of transmitted light), received by the reception portion 15, into information regarding the concentration or the amount of hemoglobin.

The display portion has a function of displaying display information based on the information to specify a change corresponding to an increase or a decrease in the concentration or the amount of hemoglobin in blood based on the light intensity, received by the reception portion 15. For example, the display portion displays display information based on the information regarding a detection result of the light intensity (intensity of transmitted light), received by the reception portion 15.

The determination portion has a function of determining whether or not the output information based on the information to specify a change corresponding to an increase or a decrease in the concentration or the amount of hemoglobin in blood based on the light intensity, received by the reception portion 15, exceeds a predetermined reference value. For example, when determination portion determines that the output information based on the information regarding a detection result of the light intensity (intensity of transmitted light), received by the reception portion 15, exceeds the predetermined reference value, the output portion 16 outputs output information based on notification information for notifying the outside (for example, a medical worker) of the fact to a monitor, a speaker, or the like.

Regarding the "predetermined reference value," a change in the intensity (intensity of transmitted light) of light which is not absorbed inside the head and is transmitted may be monitored over time, and a predetermined reference may be provided in a rate of the change to be used as the predetermined reference value.

Specifically, when the biological information system 300 is applied to a subject such as a patient requiring cardiopulmonary resuscitation, a change in the intensity (intensity of transmitted light) of light not absorbed inside the head of the subject and is transmitted may be monitored over time and, when a change to an increase in the concentration or the amount of hemoglobin in blood of the head of the subject occurs according to timings at which the sternum of the subject is pressed, a change in the intensity of transmitted light appears. When a rate of the change exceeds a predetermined reference value, a medical worker may be notified of the fact by using display means, sound means or the like.

A storage portion 40 stores information acquired by each portion of the biological information output section 200. The storage portion 40 is formed of, for example, a nonvolatile semiconductor memory such as a flash memory.

Examples of Biological Information Measurement Section 100

Figure 6:
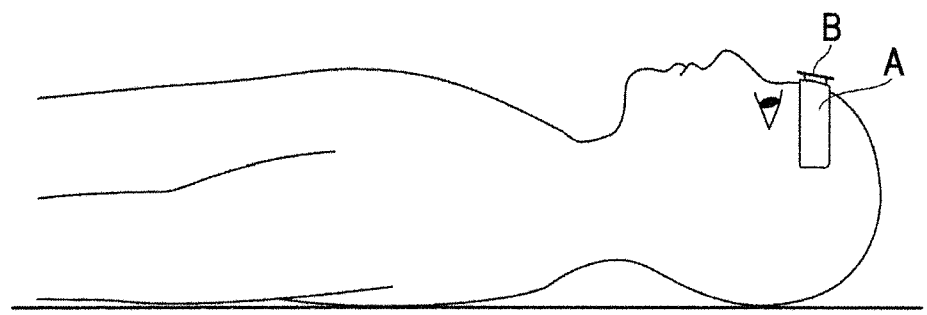
FIG. 6 is a diagram in which a state in which the biological information measurement section 100 according to the first example is attached (adhered) to the head of a subject such as a patient is viewed from the side.
Figure 7:
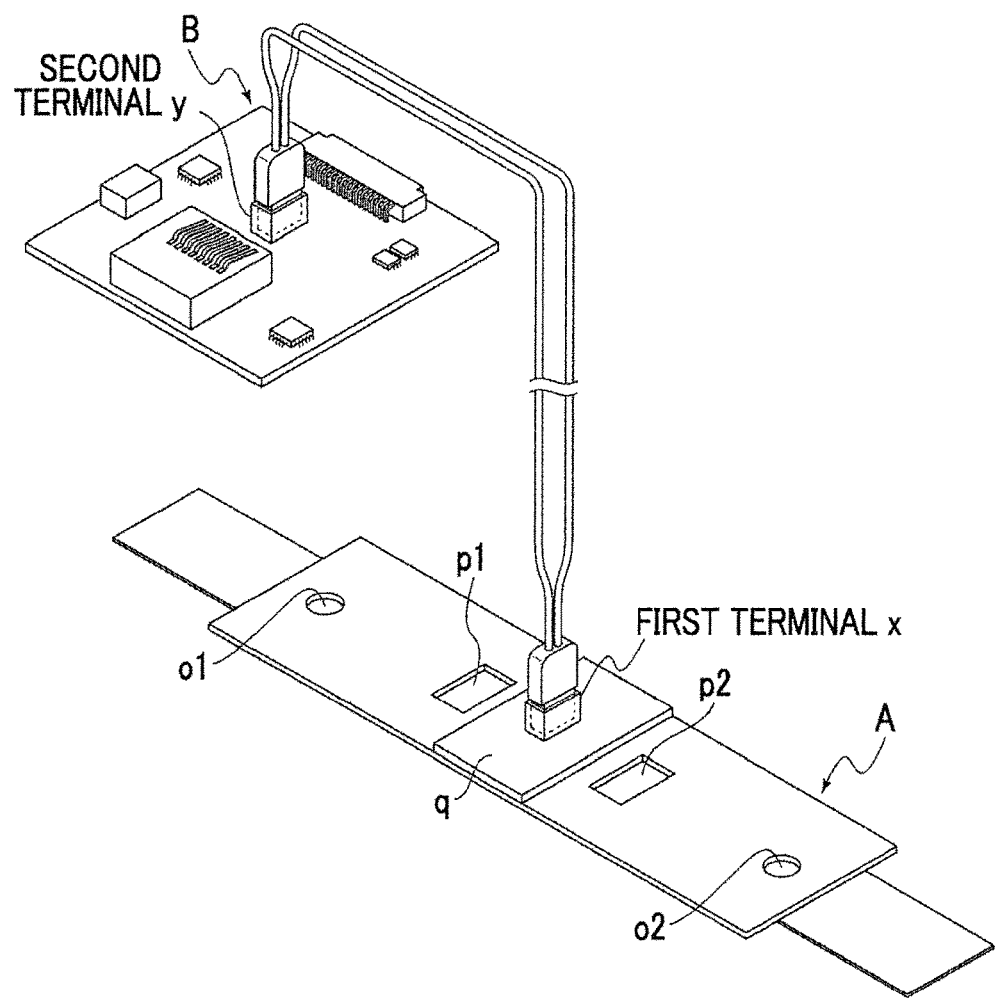
FIG. 7 is a diagram illustrating a second example of the biological information measurement section 100.
Figure 8:
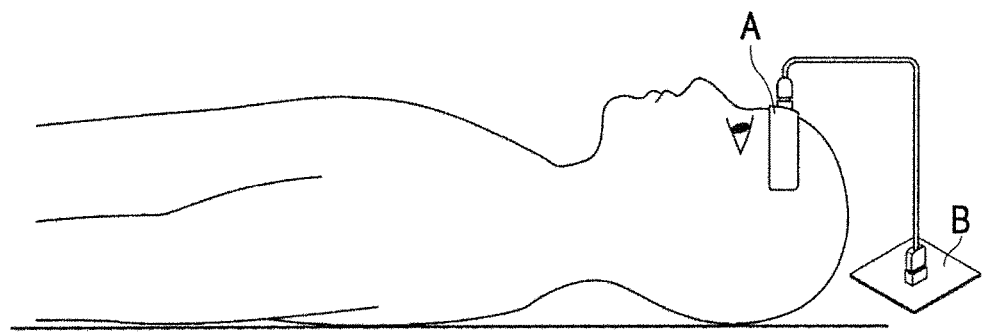
FIG. 8 is a diagram in which a state in which the biological information measurement section 100 according to the second example is attached (adhered) to the head of a subject such as a patient is viewed from the side.

An example of the biological information measurement section 100 is not particularly limited as long as the biological information measurement section can be attached (adhered) to the head of a subject such as a patient, but, a first example illustrated in FIGS. 3 and 6 and a second example illustrated in FIGS. 7 and 8 may be preferable.

Biological Information Measurement Section 100 related to First Example

Figure 3A:
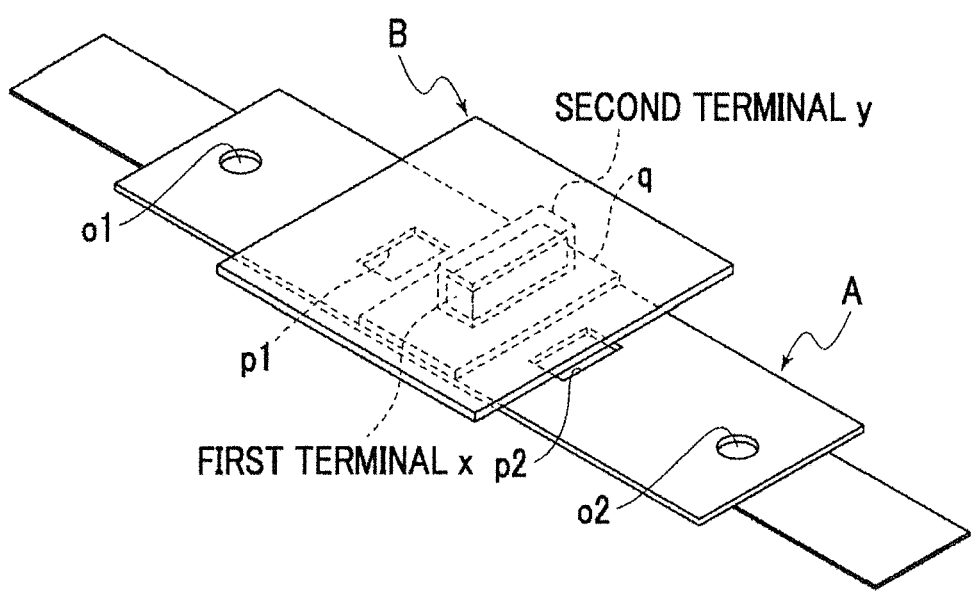
FIGS. 3A and 3B are diagrams illustrating a first example of the biological information measurement section 100.
Figure 3B:
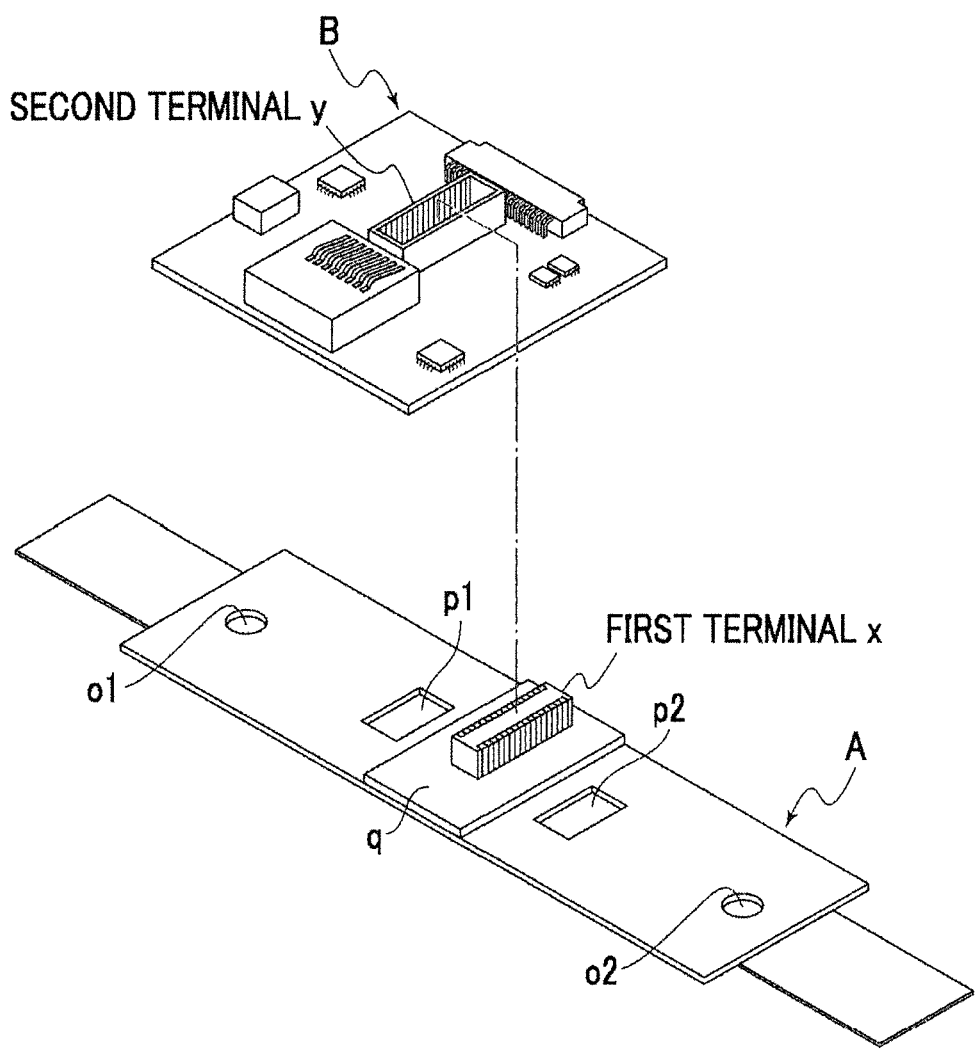

FIGS. 3A and 3B are diagrams illustrating a first example of the biological information measurement section 100.

In the biological information measurement section 100 related to the first example, a light detection unit A including the light emitting portion 11, the light receiving portion 12, and the light detection portion 13 has a first terminal x, a wireless transmission unit B including the wireless transmission portion 14 has a second terminal y, and the first terminal x and the second terminal y can be directly connected to each other in an attachable and detachable manner.

FIG. 3A is a diagram illustrating a state in which the first terminal x of the light detection unit A and the second terminal y of the wireless communication unit B directly connect to each other.

FIG. 3B is a diagram illustrating a state before the first terminal x of the light detection unit A and the second terminal y of the wireless communication unit B directly connect to each other.

FIG. 6 is a diagram in which a state in which the biological information measurement section 100 according to the first example is attached (adhered) to the head of a subject such as a patient is viewed from the side.

The biological information measurement section 100 related to the first example, illustrated in FIGS. 3a and 6 has a form in which the first terminal x of the light detection unit A and the second terminal y of the wireless transmission unit B are directly connected to each other.

Shapes of the first terminal x and the second terminal y are not particularly limited as long as the terminals can be directly connected to each other.

In the biological information measurement section 100 related to the first example, as illustrated in FIG. 3, the first terminal x of the light detection unit A and the second terminal y of the wireless transmission unit B connect to each other so that the light detection unit A and the wireless transmission unit B are integrated with each other as illustrated in FIG. 6, and thus it is possible to measure biological information by attaching (adhering) the biological information measurement section 100 to the head of a subject such as a patient.

In the biological information measurement system 300 including the biological information measurement section 100 related to the first example and the biological information output section 200, measurement information obtained by the biological information measurement section 100 can be wirelessly transmitted to the biological information output section 200 without using a communication cable between the biological information measurement section 100 and the biological information output section 200. Consequently, when a medical worker performs measurement of biological information on a subject such as a patient, the medical worker can easily perform smooth medical practice.

In the biological information measurement section 100 related to the first example, since the light detection unit A and the wireless transmission unit B are integrated with each other, when a medical worker performs measurement of biological information on a subject such as a patient, a restriction imposed on a posture of the subject such as a patient during measurement can be alleviated so that the subject can take a free posture to some degree, and thus a burden placed on the subject such as a patient during measurement can be reduced.

Biological Information Measurement Section 100 related to Second Example

FIG. 7 is a diagram illustrating a second example of the biological information measurement section 100.

In the biological information measurement section 100 related to the second example, a light detection unit A including the light emitting portion 11, the light receiving portion 12, and the light detection portion 13 has a first terminal x, a wireless transmission unit B including the wireless transmission portion 14 has a second terminal y, and the first terminal x and the second terminal y can be connected to each other via a wire.

FIG. 8 is a diagram in which a state in which the biological information measurement section 100 according to the second example is attached (adhered) to the head of a subject such as a patient is viewed from the side.

The biological information measurement section 100 related to the second example, illustrated in FIGS. 7 and 8 has a form in which the first terminal x of the light detection unit A and the second terminal y of the wireless transmission unit B are connected to each other via a wire.

Shapes of the first terminal x and the second terminal y are not particularly limited as long as the terminals can be connected to each other via a wire.

In the biological information measurement section 100 related to the second example, as illustrated in FIG. 7, the first terminal x of the light detection unit A and the second terminal y of the wireless transmission unit B are connected to each other via a wire so that the light detection unit A and the wireless transmission unit B are separate from each other as illustrated in FIG. 8, and thus it is possible to measure biological information by attaching (adhering) the biological information measurement section 100 to the head of a subject such as a patient.

In the biological information measurement system 300 including the biological information measurement section 100 related to the second example and the biological information output section 200, in the same manner as in the biological information measurement section 100 related to the first example, measurement information obtained by the biological information measurement section 100 can be wirelessly transmitted to the biological information output section 200 without using a communication cable between the biological information measurement section 100 and the biological information output section 200. Consequently, when a medical worker performs measurement of biological information on a subject such as a patient, the medical worker can easily perform smooth medical practice.

In the biological information measurement section 100 related to the second example, since the light detection unit A and the wireless transmission unit B are separate from each other, when a medical worker performs measurement of biological information on a subject such as a patient, for example, continuously for a long period of time such as sleeping, a weight is applied to the head of the subject such as a patient by only the light detection unit A, and the wireless transmission unit B is placed beside the subject such as a patient so that a burden placed on the head of the subject such as a patient during continuous measurement for a long period of time such as sleeping can be reduced.

Details of Biological Information Measurement System including Biological Information Measurement Section and Biological Information Output Section A configuration of the light emitting portion 11 is not particularly limited as long as the light emitting portion can irradiate the head of a subject such as a patient with near-infrared light in a near-infrared region, and may be a configuration in which, for example, light emitting elements such as light emitting diodes (LEDs) are provided on element boards (not illustrated), and the element boards are respectively installed at installation positions of (left) and o2 (right) illustrated in FIG. 3.

A method of irradiating the head of a subject with near-infrared light is not particularly limited, but irradiation (lighting) is preferably performed in a predetermined order by using near-infrared light beams respectively having three different wavelengths (a first wavelength $\lambda_1$ (770 nm±20 nm), a second wavelength $\lambda_2$ (805 nm±20 nm), and a third wavelength $\lambda_3$ (870 nm±20 nm)).

The first wavelength $\lambda_1$ (770 nm±20 nm) and the third wavelength $\lambda_3$ (870 nm±20 nm) are irradiation wavelengths used to calculate $rSO_2$ (oxygen saturation).

On the other hand, the second wavelength $\lambda_2$ (805 nm±20 nm) is an irradiation wavelength used to calculate a hemoglobin index (HbI).

$rSO_2$ (oxygen saturation) is preferably calculated by using two wavelengths (the first wavelength $\lambda_1$ and the third wavelength $\lambda_3$), but may be calculated by using only either one (the first wavelength $\lambda_1$ or the third wavelength $\lambda_3$) of the wavelengths.

Figure 4:
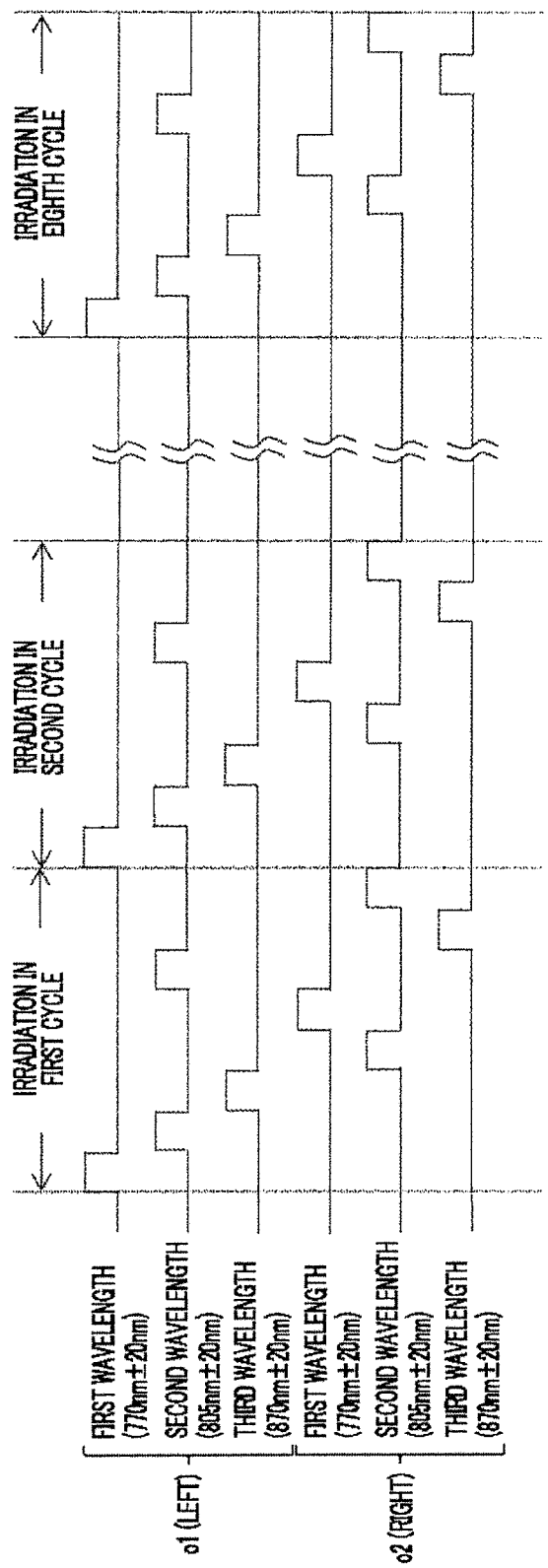
FIG. 4 is a diagram illustrating the order of applying near-infrared light having three different wavelengths (a first wavelength $\lambda_1$, a second wavelength $\lambda_2$, and a third wavelength $\lambda_3$) eight times every cycle in a time series.

FIG. 4 is a diagram illustrating the order of applying near-infrared light beams respectively having different wavelengths (the first wavelength $\lambda_1$, the second wavelength $\lambda_2$, and the third wavelength $\lambda_3$) eight times every cycle in a time series.

Figure 5:
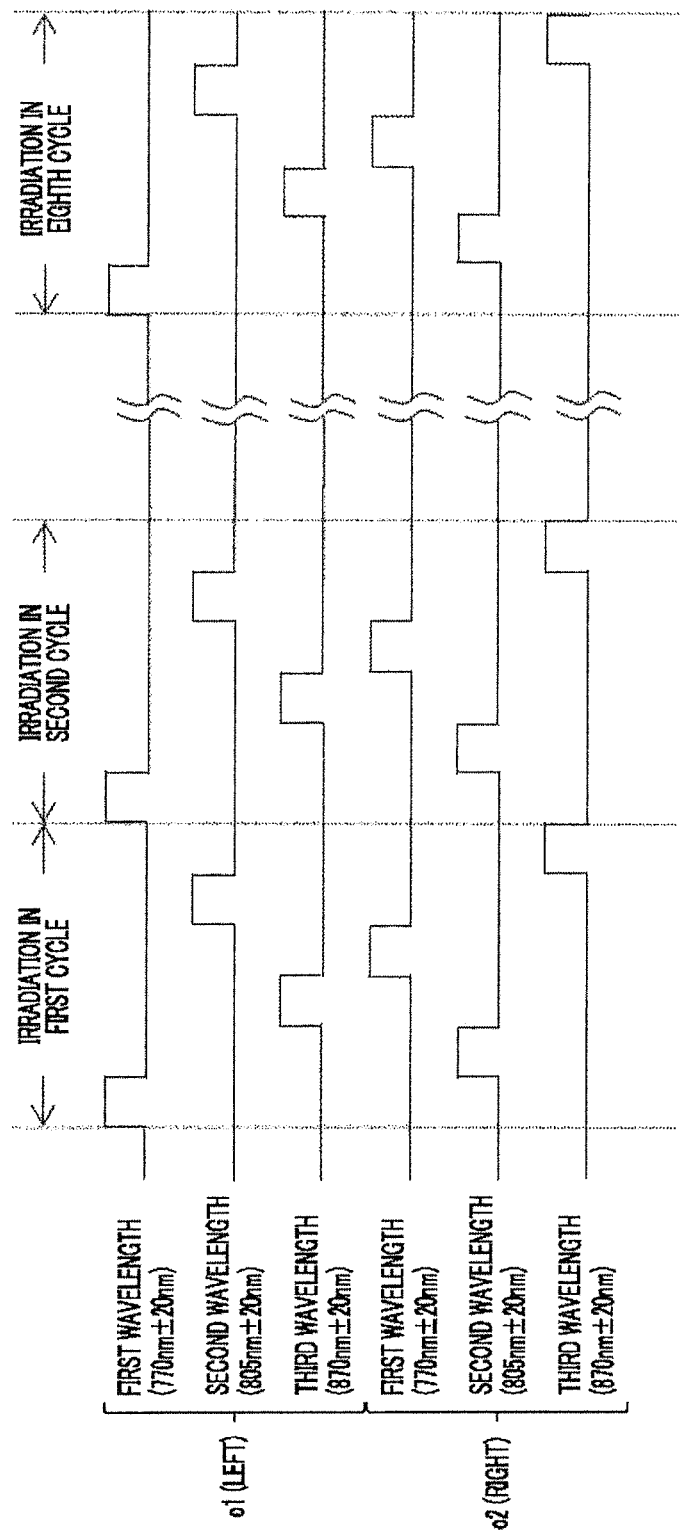
FIG. 5 is a diagram illustrating the order of applying near-infrared light having three different wavelengths (the first wavelength $\lambda_1$, the second wavelength $\lambda_2$, and the third wavelength $\lambda_3$) six times every cycle in a time series.

FIG. 5 is a diagram illustrating the order of applying near-infrared light beams respectively having different wavelengths (the first wavelength $\lambda_1$, the second wavelength $\lambda_2$, and the third wavelength $\lambda_3$) six times every cycle in a time series.

The number of times of irradiation performed in one cycle is not particularly limited, but when the number of times of irradiation is eight is more preferable than when the number of times of irradiation is six from the viewpoint of obtaining data with high reliability.

As illustrated in FIG. 4, when the number of times of irradiation is eight, irradiation using three different wavelengths (the first wavelength $\lambda_1$, the second wavelength $\lambda_2$, and the third wavelength $\lambda_3$) is performed eight times in a predetermined order in a first cycle, and is performed eight times in a second cycle and the subsequent cycles in the same order as the order in the first cycle. This irradiation repeatedly performed until an eighth cycle is regarded as one set, and irradiation is preferably performed for one or more sets.

The order of eight times of irradiation performed in the first cycle is the order of "A→B→C→D→E→F→G→H" as follows (first aspect):

First Aspect of Order of Eight Times of Irradiation
A: o1 (left) first wavelength $\lambda_1$ (770 nm±20 nm)
B: o1 (left) second wavelength $\lambda_2$ (805 nm±20 nm)
C: o1 (left) third wavelength $\lambda_3$ (870 nm±20 nm)
D: o2 (right) second wavelength $\lambda_2$ (805 nm±20 nm)
E: o2 (right) first wavelength $\lambda_1$ (770 nm±20 nm)
F: o1 (left) second wavelength $\lambda_2$ (805 nm±20 nm)
G: o2 (right) third wavelength $\lambda_3$ (870 nm±20 nm)
H: o2 (right) second wavelength $\lambda_2$ (805 nm±20 nm).

Since both of the first wavelength $\lambda_1$ (770 nm±20 nm) and the third wavelength $\lambda_3$ (870 nm±20 nm) are irradiation wavelengths used to calculate $rSO_2$ (oxygen saturation), irradiation may be performed in the following order by replacing the orders of the first wavelength $\lambda_1$ (770 nm±20 nm) and the third wavelength $\lambda_3$ (870 nm±20 nm) with each other (second aspect):

Second Aspect of Order of Eight Times of Irradiation
A: o1 (left) third wavelength $\lambda_3$ (870 nm±20 nm)
B: o1 (left) second wavelength $\lambda_2$ (805 nm±20 nm)
C: o1 (left) first wavelength $\lambda_1$ (770 nm±20 nm)
D: o2 (right) second wavelength $\lambda_2$ (805 nm±20 nm)
E: o2 (right) third wavelength $\lambda_3$ (870 nm±20 nm)
F: o1 (left) second wavelength $\lambda_2$ (805 nm±20 nm)
G: o2 (right) first wavelength $\lambda_1$ (770 nm±20 nm)
H: o2 (right) second wavelength $\lambda_2$ (805 nm±20 nm).

In the first and second aspects of the order of eight times of irradiation, the first irradiation is started from "A," but irradiation may be started from any one of "B" to "H." When irradiation is started from orders other than "A," irradiation is performed according to "A" following "H."

For example, when the first irradiation is started from "C," eight times of irradiation is performed in the order of "C→D→E→F→G→H→A→B."

As described above, when irradiation is performed eight times every cycle, irradiation from the first cycle to the eighth cycle, that is, a total of 64 times of irradiation is regarded as one set, and irradiation is preferably performed for one or more sets. At least one set of irradiation (64 times of irradiation in eight cycles) is preferably performed within one second.

For example, four sets of irradiation (256 times of irradiation in 32 cycles) may be performed within one second.

The irradiation time of one second for which at least one set of irradiation is performed also includes an irradiation standby time, and the time required for one time of irradiation using each of three different wavelengths (the first wavelength $\lambda_1$, the second wavelength $\lambda_2$, and the third wavelength $\lambda_3$) is actually about 90 to 180 μsec.

Eight times of irradiation performed in one cycle is preferable from the viewpoint of obtaining data with reliability, but six times of irradiation may be employed.

As illustrated in FIG. 5, when the number of times of irradiation is eight, irradiation using three different wavelengths (the first wavelength $\lambda_1$, the second wavelength $\lambda_2$, and the third wavelength $\lambda_3$) is performed six times in a predetermined order in a first cycle, and is performed eight times in a second cycle and the subsequent cycles in the same order as the order in the first cycle. This irradiation repeatedly performed until an eighth cycle is regarded as one set, and irradiation is preferably performed for one or more sets.

The order of six times of irradiation performed in the first cycle is the order of "A→B→C→D→E→F" as follows:
Order of Six Times of Irradiation
A: o1 (left) first wavelength $\lambda_1$ (770 nm±20 nm)
B: o2 (right) second wavelength $\lambda_2$ (805 nm±20 nm)
C: o1 (left) third wavelength $\lambda_3$ (870 nm±20 nm)
D: o2 (right) first wavelength $\lambda_1$ (770 nm±20 nm)
E: o1 (left) second wavelength $\lambda_2$ (805 nm±20 nm)
F: o2 (right) third wavelength $\lambda_3$ (870 nm±20 nm).

The second wavelength $\lambda_2$ (805 nm±20 nm) is an irradiation wavelength used to calculate a hemoglobin index (HbI), and irradiation using the wavelength is performed twice for each of the left and right in eight times of irradiation illustrated in FIG. 4, but irradiation may be performed once for each of the left and right in six times of irradiation illustrated in FIG. 5.

In the order of six times of irradiation, the first irradiation is started from "A," but irradiation may be started from any one of "B" to "F." When irradiation is started from orders other than "A," irradiation is performed according to "A" following "F."

For example, when the first irradiation is started from "C," six times of irradiation is performed in the order of "C→D→E→F→A→B."

As described above, when irradiation is performed six times every cycle, irradiation from the first cycle to the eighth cycle, that is, a total of 48 times of irradiation is regarded as one set, and irradiation is preferably performed for one or more sets. At least one set of irradiation (48 times of irradiation in eight cycles) is preferably performed within one second.

For example, four sets of irradiation (144 times of irradiation in 24 cycles) may be performed within one second.

The irradiation time of one second for which at least one set of irradiation is performed also includes an irradiation standby time, and the time required for one time of irradiation using each of three different wavelengths (the first wavelength $\lambda_1$, the second wavelength $\lambda_2$, and the third wavelength $\lambda_3$) is actually about 90 to 180 μsec.

A configuration of the light receiving portion 12 is not particularly limited as long as the light receiving portion can receive light as a result of near-infrared light applied from the light emitting portion 11 propagating inside the head of a subject, and may be a configuration in which, for example, light receiving elements such as photodiodes (PDs) are provided on element boards (not illustrated), and the element boards are respectively installed at installation positions p1 (left) and p2 (right) illustrated in FIG. 3.

The "light propagating inside the head of a subject" indicates light (transmitted light) as a result of near-infrared light irradiated from the light emitting portion 11 transmitted without being absorbed inside the head.

The light receiving portion 12 may be appropriately designed to receive light in synchronization with an irradiation timing of near-infrared light and receive light (transmitted light) not absorbed inside the head and transmitted without missing the light.

As described above, also when the light emitting portion 11 performs irradiation (lighting) with near-infrared light beams respectively having three different wavelengths (the first wavelength $\lambda_1$ (770 nm±20 nm), the second wavelength $\lambda_2$ (805 nm±20 nm), and the third wavelength $\lambda_3$ (870 nm±20 nm)) in a predetermined order, the light receiving portion 12 can receive light beams as a result of the near-infrared light beams respectively having the three different wavelengths (the first wavelength $\lambda_1$ (770 nm±20 nm), the second wavelength $\lambda_2$ (805 nm±20 nm), and the third wavelength $\lambda_3$ (870 nm±20 nm)) applied from the light emitting portion 11 in the predetermined order propagating inside the head of a subject.

A configuration of the light detection portion 13 is not particularly limited as long as the light detection portion can detect the intensity of light received by the light receiving portion 12, and may be a configuration in which, for example, a light detector which detects the intensity of light detected by the light receiving portion 12, that is, the intensity (intensity of transmitted light) of light transmitted inside the head of a subject is provided on a board (not illustrated), and the board is installed at an installation position q illustrated in FIG. 3.

As described above, also when the light receiving portion 12 receives light beams as a result of near-infrared light beams respectively having three different wavelengths (the first wavelength $\lambda_1$ (770 nm±20 nm), the second wavelength $\lambda_2$ (805 nm±20 nm), and the third wavelength $\lambda_3$ (870 nm±20 nm)) propagating inside the head of a subject, the light detection portion 13, the light detection portion 13 can detect the intensities of the respective light beams received from the light receiving portion 12, that is, the intensities (intensity of transmitted light) of light beams transmitted inside the head of the subject.

A configuration of the wireless transmission portion 14 is not particularly limited as long as the wireless transmission portion can wirelessly transmit information to specify a change corresponding to an increase or a decrease in the concentration or the amount of hemoglobin in blood based on the light intensity detected by the light detection portion 13, and a device that can perform wireless transmission may be provided in the wireless transmission unit B of the biological information measurement section 100, and a Bluetooth (registered trademark) method may be employed.

The "information to specify a change corresponding to an increase or a decrease in the concentration or the amount of hemoglobin" may be information regarding a detection result of the light intensity (intensity of transmitted light) detected by the light detection portion 13, or may be information regarding a result obtained by converting the information regarding a detection result of the light intensity (intensity of transmitted light) detected by the light detection portion 13 into the concentration or the amount of hemoglobin.

The biological information measurement section 100 may include a calculation portion. A configuration of the calculation portion is not limited as long as the calculation portion can perform a calculation process on information to specify a change corresponding to an increase or a decrease in the concentration or the amount of hemoglobin in blood based on the light intensity detected by the light detection portion 13.

For example, the calculation portion performs a calculation process to convert information regarding a detection result of the light intensity (intensity of transmitted light) detected by the light detection portion 13 into information regarding the concentration or the amount of hemoglobin. Alternatively, the calculation portion performs a calculation process to generate information regarding a detection result of the light intensity (intensity of transmitted light) detected by the light detection portion 13 as numerical values or images.

Since the biological information measurement section 100 includes the calculation portion, an amount of information wirelessly transmitted by the wireless transmission portion 14 or an amount of information received by the reception portion 15 can be reduced, and thus a burden placed on the wireless transmission portion 14 and the reception portion 15 can be reduced so that the time required for wireless transmission and wireless reception can be reduced.

The biological information measurement section 100 may include a display portion. A configuration of the display portion is not limited as long as the display portion can perform display of display information based on the information to specify a change corresponding to an increase or a decrease in the concentration or the amount of hemoglobin in blood based on the light intensity detected by the light detection portion 13 and, for example, the biological information measurement section 100 may be provided with a monitor or the like.

For example, the display portion displays display information based on the information regarding a detection result of the light intensity (intensity of transmitted light) detected by the light detection portion 13 on a monitor or the like. Alternatively, the display portion displays display information based on information regarding a result of a calculation process in the calculation portion to convert information regarding a detection result of the light intensity (intensity of transmitted light) detected by the light detection portion 13 into information regarding the concentration or the amount of hemoglobin. Alternatively, the display portion displays display information based on information regarding a result of a calculation process in the calculation portion to generate information regarding a detection result of the light intensity (intensity of transmitted light) detected by the light detection portion 13 as numerical values or images.

Since the biological information measurement section 100 includes the display portion, when a medical worker performs other medical practice while measuring biological information of a subject such as a patient, the medical worker can accurately perform other medical practice while checking a change (a change in a blood flow) in an amount of blood flowing inside the head of the subject in real time by using not only the biological information output section 200 but also the biological information measurement section 100.

A configuration of the reception portion 15 is not particularly limited as long as the reception portion can wirelessly receive information to specify a change corresponding to an increase or a decrease in the concentration or the amount of hemoglobin in blood based the light intensity, wirelessly transmitted from the wireless transmission portion 14 of the biological information measurement section 100 and, for example, a device that can perform wireless reception may be provided in the biological information output section 200, and a Bluetooth (registered trademark) method may be employed.

A configuration of the output portion 16 is not particularly limited as long as the output portion can perform outputting of output information based on the information to specify a change corresponding to an increase or a decrease in the concentration or the amount of hemoglobin in blood based on the light intensity, received by the reception portion 15, and the output portion outputs the output information based on information regarding a detection result of the light intensity (intensity of transmitted light), received by the reception portion 15, visually with a monitor or the like, or auditorily with a speaker, or the like.

An example of the monitor may include a small-sized and lightweight communication apparatus such as a smart phone. An aspect may also be realized in which output information which is output from the small-sized and lightweight communication apparatus may be transmitted to other communication apparatuses.

The biological information output section 200 may also include a calculation portion in the same manner as the above-described biological information measurement section 100. A configuration of the calculation portion is not limited as long as the calculation portion can perform a calculation process on information to specify a change corresponding to an increase or a decrease in the concentration or the amount of hemoglobin in blood based on the light intensity, received by the reception portion 15.

For example, the calculation portion performs a calculation process to convert information regarding a detection result of the light intensity (intensity of transmitted light), received by the reception portion 15, into information regarding the concentration or the amount of hemoglobin. Alternatively, the calculation portion performs a calculation process to generate information regarding a detection result of the light intensity (intensity of transmitted light), received by the reception portion 15, as numerical values or images.

Since the biological information output section 200 includes the calculation portion, the biological information output section 200 performs a calculation process on information regarding a detection result of the light intensity (intensity of transmitted light), received by the reception portion 15, and thus the biological information measurement section 100 is made to have a calculation process function, or the calculation process function of the biological information measurement section 100 can be restricted. Therefore, the biological information measurement section 100 can be designed to be small-sized and lightweight.

The biological information output section 200 may also include a display portion in the same manner as the biological information measurement section 100. A configuration of the display portion is not limited as long as the display portion can perform display of display information based on the information to specify a change corresponding to an increase or a decrease in the concentration or the amount of hemoglobin in blood based on the light intensity, received by the reception portion 15, and, for example, the biological information output section 200 may be provided with a monitor or the like.

For example, the display portion displays display information based on the information regarding a detection result of the light intensity (intensity of transmitted light), received by the reception portion 15, on a monitor or the like. Alternatively, the display portion displays display information based on information regarding a result of a calculation process in the calculation portion to convert information regarding a detection result of the light intensity (intensity of transmitted light), received by the reception portion 15, into information regarding the concentration or the amount of hemoglobin. Alternatively, the display portion displays display information based on information regarding a result of a calculation process in the calculation portion to convert information regarding a detection result of the light intensity (intensity of transmitted light), received by the reception portion 15, as numerical values or images.

Since the biological information output section 200 includes the display portion, when a medical worker performs other medical practice while measuring biological information of a subject such as a patient, the medical worker can accurately perform other medical practice while checking a change (a change in a blood flow) in an amount of blood flowing inside the head of the subject in real time by using the display portion provided in the biological information output section 200.

The biological information output section 200 may include a determination portion. The determination portion may determine whether or not there is a change in information regarding a change in a blood flow, that is, a blood flow changes on the basis of the information to specify a change corresponding to an increase or a decrease in the concentration or the amount of hemoglobin in blood based on the light intensity.

According to a method of determining whether or not a blood flow changes, in a light emitting portion on o1 (left) and a light receiving portion on P1 (left) forming a pair, and a light emitting portion on o2 (right) and a light receiving portion on P2 (right) forming a pair, light beams having respective wavelengths (the first wavelength $\lambda_1$, the second wavelength $\lambda_2$, or the third wavelength $\lambda_3$) are applied from the light emitting portions on o1 (left) and o2 (right) in a predetermined order, and the light detection portion detects the intensities (intensity of transmitted light) of light beams respectively received by the light receiving portions on p1 (left) and p2 (right).

In respective pieces of data detected by the light detection portion in each cycle, when differences between pieces of data are all laid in the same direction (for example, all in an increase direction) through comparison between adjacent cycles (for example, a first cycle and a second cycle), whereas differences between pieces of data are all laid in an opposite direction (for example, all in a decrease direction) through comparison between other adjacent cycles (for example, a third cycle and a fourth cycle), it may be determined that a blood flow changes.

Specifically, according to the method of determining whether or not blood flow changes described below, when (i) the light emitting portion on o1 (left) applies light beams having respective wavelengths (the first wavelength $\lambda_1$, the second wavelength $\lambda_2$, and the third wavelength $\lambda_3$), and pieces of data obtained by the light detection portion detecting the intensities of light beams received by the light receiving portion on p1 (left) satisfy all of tendencies of (1) to (3), and (ii) the light emitting portion on o2 (right) applies light beams having respective wavelengths (the first wavelength $\lambda_1$, the second wavelength $\lambda_2$, and the third wavelength $\lambda_3$), and pieces of data obtained by the light detection portion detecting the intensities (intensity of transmitted light) of light beams received by the light receiving portion on p2 (right) satisfy all of tendencies of (4) to (6), it may be determined that a blood flow changes.

Conversely, if at least one of a total of six tendencies (i) of (1) to (3) and (4) to (6) is not satisfied, it may be determined that a blood flow does not change. Method of determining whether or not blood flow changes (i) o1 (left)

(1) In pieces of data obtained by applying light having the first wavelength $\lambda_1$ and the light detection portion detecting the intensity (intensity of transmitted light) of light received by the light receiving portion on p1 (left) in each cycle, a difference between pieces of data based on comparison between the first cycle and the second cycle increases, whereas a difference between pieces of data based on comparison between the third cycle and the fourth cycle decreases.

(2) In pieces of data obtained by applying light having the second wavelength $\lambda_2$ and the light detection portion detecting the intensity (intensity of transmitted light) of light received by the light receiving portion on p1 (left) in each cycle, a difference between pieces of data based on comparison between the first cycle and the second cycle increases, whereas a difference between pieces of data based on comparison between the third cycle and the fourth cycle decreases.

(3) In pieces of data obtained by applying light having the third wavelength $\lambda_3$ and the light detection portion detecting the intensity (intensity of transmitted light) of light received by the light receiving portion on p1 (left) in each cycle, a difference between pieces of data based on comparison between the first cycle and the second cycle increases, whereas a difference between pieces of data based on comparison between the third cycle and the fourth cycle decreases.

(ii) o2 (right)

(4) In pieces of data obtained by applying light having the first wavelength $\lambda_1$ and the light detection portion detecting the intensity (intensity of transmitted light) of light received by the light receiving portion on p1 (left) in each cycle, a difference between pieces of data based on comparison between the first cycle and the second cycle increases, whereas a difference between pieces of data based on comparison between the third cycle and the fourth cycle decreases.

(5) In pieces of data obtained by applying light having the second wavelength $\lambda_2$ and the light detection portion detecting the intensity (intensity of transmitted light) of light received by the light receiving portion on p1 (left) in each cycle, a difference between pieces of data based on comparison between the first cycle and the second cycle increases, whereas a difference between pieces of data based on comparison between the third cycle and the fourth cycle decreases.

(6) In pieces of data obtained by applying light having the third wavelength $\lambda_3$ and the light detection portion detecting the intensity (intensity of transmitted light) of light received by the light receiving portion on p1 (left) in each cycle, a difference between pieces of data based on comparison between the first cycle and the second cycle increases, whereas a difference between pieces of data based on comparison between the third cycle and the fourth cycle decreases.

In the above method of determining whether or not blood flow changes, the first cycle and the second cycle are used as examples of adjacent cycles, the third cycle and the fourth cycle are used as examples other adjacent cycles, but these are only examples.

As described above, it is possible to obtain data with high reliability by performing irradiation (lighting) in a predetermined order by using near-infrared light beams respectively having three different wavelengths (the first wavelength $\lambda_1$ (770 nm±20 nm), the second wavelength $\lambda_2$ (805 nm±20 nm), and the third wavelength $\lambda_3$ (870 nm±20 nm)).

It is possible to accurately determine whether or not there is a change in a blood flow according to the above-described method of determining whether or not a blood flow changes on the basis of the data with high reliability.

Thus, even if a subject' body is shaken due to pressing of the sternum of the subject, it is possible to accurately determine even a minute change in a blood flow without being influenced much by the shaking on the basis of the data with high reliability.

The determination portion monitors information regarding a change in a blood flow based on information for specifying a change corresponding to an increase or a decrease in the concentration or the amount of hemoglobin in blood based on the light intensity, received by the reception portion 15, over time, and determines whether or not a rate of the change in a blood flow exceeds a predetermined reference value in a case where there is a change in the information regarding a change in a blood flow according to a timing of chest compressions of a subject.

The "information regarding a change in a blood flow based on information to specify a change corresponding to an increase or a decrease in the concentration or the amount of hemoglobin in blood based on the light intensity" may be, for example, (1) output information based on information regarding a detection result of the light intensity (intensity of transmitted light), (2) output information based on information regarding a result of a calculation process performed in the calculation portion to convert information regarding a detection result of the light intensity (intensity of transmitted light) into information regarding the concentration or the amount of hemoglobin, and (3) output information based on information regarding a result of a calculation process in the calculation portion performed to generate information regarding a detection result of the light intensity (intensity of transmitted light) as numerical values or images.

The above-described determination portion has been described to be included in the biological information output section 200, but a determination portion may also be included in the biological information measurement section 100.

When the determination portion determines that information regarding a change in a blood flow based on information for specifying a change corresponding to an increase or a decrease in the concentration or the amount of hemoglobin in blood based on the light intensity, received by the reception portion 15, exceeds the predetermined reference value, the biological information output section 200 outputs output information based on notification information to notify the outside (for example, a medical worker) of the fact to a monitor, a speaker or the like. Consequently, the medical worker can accurately perform medical practice on the basis of the notification information output from the biological information output section 200.

When the determination portion determines that information regarding a change in a blood flow exceeds a predetermined reference value, the biological information output section 200 notifies the outside of the fact and, similarly, when the determination portion determines that information regarding a change in a blood flow exceeds a predetermined reference value, the biological information measurement section 100 may notify the outside of the fact.

Process Performed by Biological Information Measurement System 300

FIG. 9 is a flowchart illustrating an example of a process performed by the biological information measurement system 300 including the biological information measurement section 100 and the biological information output section 200. FIG. 9 is a flowchart corresponding to the block diagram in FIG. 2.

In the following description, "step" in a parenthesis indicates each step executed by the biological information measurement section 100 and the biological information output section 200.

A process performed by the biological information measurement system 300 is realized through respective steps exemplified in FIG. 9.

The head of a subject is irradiated with near-infrared light (step 1 (S1); hereinafter, a "step" is abbreviated to "S"; a light emission step), and the head of the subject is irradiated with near-infrared light from the lighting step (S2; light reception step).

The intensity of light received in the light reception step is detected (S3; light detection step), and information to specify a change corresponding to an increase or a decrease in the concentration or the amount of hemoglobin in blood based on the light intensity detected in the light detection step is wirelessly transmitted (S4; wireless transmission step).

Next, the information to specify a change corresponding to an increase or a decrease in the concentration or the amount of hemoglobin in blood based on the light intensity, wirelessly transmitted from the wireless transmission step, is received (S5; reception step), and output information based on the information to specify a change corresponding to an increase or a decrease in the concentration or the amount of hemoglobin in blood based on the light intensity, received in the reception step, is output (S6; output step).

INDUSTRIAL APPLICABILITY

My systems and methods are not limited to the above-described examples, and may be variously modified within the scope in the appended claims, examples obtained by combining the technical means disclosed in different examples with each other as appropriate are also included in the technical scope of this disclosure. A novel technical feature can be formed by combining the technical means disclosed in the respective examples with each other.

The invention claimed is:

1. A biological information measurement system applied to a subject requiring cardiopulmonary resuscitation, comprising:
    a biological information measurement section; and
    a biological information output section,
    wherein the biological information measurement section comprises:
        a light emitting portion configured to irradiate the head of the subject with near-infrared light,
        a light receiving portion configured to receive light as a result of the near-infrared light applied from the light emitting portion propagating inside the head of the subject,
        a light detection portion that detects the intensity of the light received by the light receiving portion, and
        a wireless transmission portion that wirelessly transmits information to specify a change corresponding to an increase or a decrease in the concentration or the amount of hemoglobin in blood based on the light intensity detected by the light detection portion, and wherein the biological information output section comprises:
a reception portion that receives the information to specify a change corresponding to an increase or a decrease in the concentration or the amount of hemoglobin, wirelessly transmitted from the wireless transmission portion of the biological information measurement section, and
a determination portion that monitors information regarding a change in a blood flow based on the information to specify a change corresponding to an increase or a decrease in the concentration or the amount of hemoglobin in blood based on the light intensity, received by the reception portion, over time, and determines whether or not a rate of the change in a blood flow exceeds a predetermined reference value when there is a change in the information regarding a change in a blood flow according to a timing of chest compressions of the subject, wherein
the biological information output section further comprises:
a calculation portion that performs a calculation process on the information to specify a change corresponding to an increase or a decrease in the concentration or the amount of hemoglobin, received by the reception portion, and
when the determination portion determines that the predetermined reference value is exceeded, the biological information output section outputs output information based on notification information to notify the outside that the predetermined reference value is exceeded,
wherein the light emitting portion of the biological information measurement section irradiates the head of the subject with near-infrared light having three different wavelengths, and the three different wavelengths are a first wavelength $\lambda_1$ (770 nm±20 nm), a second wavelength $\lambda_2$ (805 nm±20 nm), and a third wavelength $\lambda_3$ (870 nm±20 nm), and
the light emitting portion and the light receiving portion of the biological information measurement section include a light emitting portion (o1) and a light receiving portion (p1) for performing measurement, provided on the left as a pair, and a light emitting portion (o2) and a light receiving portion (p2) for performing measurement, provided on the right as a pair, and the order of eight times of irradiation performed every cycle by using near-infrared light having three different wavelengths is any one of the following orders of A→B→C→D→E→F→G→H, B→C→D→E→F→G→H→A, C→D→E→F→G→H→A→B, D→E→F→G→H→A→B→C, E→F→G→H→A→B→C→D, F→G→H→A→B→C→D→E, G→H→A→B→C→D→E→F, and H→A→B→C→D→E→F→G:
A: o1 (left) first wavelength $\lambda_1$ (770 nm±20 nm)
B: o1 (left) second wavelength $\lambda_2$ (805 nm±20 nm)
C: o1 (left) third wavelength $\lambda_3$ (870 nm±20 nm)
D: o2 (right) second wavelength $\lambda_2$ (805 nm±20 nm)
E: o2 (right) first wavelength $\lambda_1$ (770 nm±20 nm)
F: o1 (left) second wavelength $\lambda_2$ (805 nm±20 nm)
G: o2 (right) third wavelength $\lambda_3$ (870 nm±20 nm)
H: o2 (right) second wavelength $\lambda_2$ (805 nm±20 nm).

2. The biological information measurement system according to claim 1,
wherein, in the biological information measurement section, a light detection unit including the light emitting portion, the light receiving portion, and the light detection portion has a first terminal, a wireless transmission unit including the wireless transmission portion has a second terminal, and the first terminal and the second terminal are directly connected to each other in an attachable and detachable manner.

3. The biological information measurement system according to claim 1,
wherein, in the biological information measurement section, a light detection unit including the light emitting portion, the light receiving portion, and the light detection portion has a first terminal, a wireless transmission unit including the wireless transmission portion has a second terminal, and the first terminal and the second terminal connect to each other via a wire.

4. The biological information measurement system according to claim 1, wherein the biological information measurement section further comprises a display portion that displays display information based on the information to specify a change corresponding to an increase or a decrease in the concentration or the amount of hemoglobin, detected by the light detection portion.

5. The biological information measurement system according to claim 1, wherein the biological information output section further comprises a display portion that displays display information based on the information to specify a change corresponding to an increase or a decrease in the concentration or the amount of hemoglobin, received by the reception portion.

6. The biological information measurement system according to claim 1, wherein the biological information measurement section further comprises a calculation portion that performs a calculation process on the information to specify a change corresponding to an increase or a decrease in the concentration or the amount of hemoglobin, detected by the light detection portion.

7. The biological information measurement system according to claim 1, wherein the light emitting portion irradiates near-infrared light having three different wavelengths.

8. The biological information measurement system according to claim 1, wherein the light emitting portion includes a left light emitting portion (o1) and a right light emitting portion (o2),
the left light emitting portion is installed at a left light emitting portion installation position in the biological information measurement section,
the right light emitting portion is installed at a right light emitting portion installation position in the biological information measurement section,
the light receiving portion includes a left light receiving portion (p1) and a right light receiving portion (p2),
the left light receiving portion is installed at a left light receiving portion installation position in the biological information measurement section, and
the right light receiving portion is installed at a right light receiving portion installation position in the biological information measurement section.

9. The biological information measurement system according to claim 8, wherein only one of the left light emitting portion (o1) and right light emitting portion (o2) irradiates at a certain timing.

10. The biological information measurement system according to claim 1, wherein the orders of A: o1 (left) first wavelength $\lambda_1$ (770 nm±20 nm) and C: o1 (left) third wavelength $\lambda_3$ (870 nm±20 nm) may be replaced with each other, or the orders of E: o2 (right) first wavelength $\lambda_1$ (770 nm±20 nm) and G: o2 (right) third wavelength $\lambda_3$ (870 nm±20 nm) may be replaced with each other.

11. A method of operating a biological information measurement system applied to a subject requiring cardiopulmonary resuscitation, comprising:
   a biological information measurement step executed in a biological information measurement section; and
   a biological information output step executed in a biological information output section,
   wherein the biological information measurement step comprises:
   a light emission step of emitting with near-infrared light,
   a light reception step of receiving light as a result of the near-infrared light applied in the light emission step propagating inside the head of the subject,
   a light detection step of detecting the intensity of the light received in the light reception step, and
   a wireless transmission step of wirelessly transmitting information specify a change corresponding to an increase or a decrease in the concentration or the amount of hemoglobin in blood based on the light intensity detected in the light detection step, and
   wherein the biological information output step comprises:
   a reception step of receiving the information to specify a change corresponding to an increase or a decrease in the concentration or the amount of hemoglobin, wirelessly transmitted in the wireless transmission step of the biological information measurement step, and
   a determination step of causing the biological information output section to monitor information regarding a change in a blood flow based on the information to specify a change corresponding to an increase or a decrease in the concentration or the amount of hemoglobin, received in the reception step, over time, and to determine whether or not a rate of the change in a blood flow exceeds a predetermined reference value when there is a change in the information regarding a change in a blood flow according to a timing of chest compressions of the subject, wherein
   the biological information output step further comprises:
   a calculation step of calculating the information to specify a change corresponding to an increase or a decrease in the concentration or the amount of hemoglobin, received in the reception step, and
   when it is determined that the predetermined reference value is exceeded in the determination step, the biological information output section outputs output information based on notification information to notify the outside that the predetermined reference value is exceeded,
   wherein the light emitting portion of the biological information measurement section irradiates the head of the subject with near-infrared light having three different wavelengths, and the three different wavelengths are a first wavelength $\lambda_1$ (770 nm±20 nm), a second wavelength $\lambda_2$ (805 nm±20 nm), and a third wavelength $\lambda_3$ (870 nm±20 nm), and
   the light emitting portion and the light receiving portion of the biological information measurement section include a light emitting portion (o1) and a light receiving portion (p1) for performing measurement, provided on the left as a pair, and a light emitting portion (o2) and a light receiving portion (p2) for performing measurement, provided on the right as a pair, and the order of eight times of irradiation performed every cycle by using near-infrared light having three different wavelengths is any one of the following orders of A→B→C→D→E→F→G→H, B→C→D→E→F→G→H→A, C→D→E→F→G→H→A→B, D→E→F→G→H→A→B→C, E→F→G→H→A→B→C→D, F→G→H→A→B→C→D→E, G→H→A→B→C→D→E→F, and H→A→B→C→D→E→F→G:
   A: o1 (left) first wavelength $\lambda_1$ (770 nm±20 nm)
   B: o1 (left) second wavelength $\lambda_2$ (805 nm±20 nm)
   C: o1 (left) third wavelength $\lambda_3$ (870 nm±20 nm)
   D: o2 (right) second wavelength $\lambda_2$ (805 nm±20 nm)
   E: o2 (right) first wavelength $\lambda_1$ (770 nm±20 nm)
   F: o1 (left) second wavelength $\lambda_2$ (805 nm±20 nm)
   G: o2 (right) third wavelength $\lambda_3$ (870 nm±20 nm)
   H: o2 (right) second wavelength $\lambda_2$ (805 nm±20 nm).

12. The method according to claim 11, wherein the light emitting portion irradiates near-infrared light having three different wavelengths.

13. The method according to claim 11, wherein the light emitting portion includes a left light emitting portion (o1) and a right light emitting portion (o2),
   the left light emitting portion is installed at a left light emitting portion installation position in the biological information measurement section,
   the right light emitting portion is installed at a right light emitting portion installation position in the biological information measurement section,
   the light receiving portion includes a left light receiving portion (p1) and a right light receiving portion (p2),
   the left light receiving portion is installed at a left light receiving portion installation position in the biological information measurement section, and
   the right light receiving portion is installed at a right light receiving portion installation position in the biological information measurement section.

14. The method according to claim 11, wherein only one of the left light emitting portion (o1) and right light emitting portion (o2) irradiates at a certain timing.

15. The method according to claim 11, wherein the orders of A: o1 (left) first wavelength $\lambda_1$ (770 nm±20 nm) and C: o1 (left) third wavelength $\lambda_3$ (870 nm±20 nm) may be replaced with each other, or the orders of E: o2 (right) first wavelength $\lambda_1$ (770 nm±20 nm) and G: o2 (right) third wavelength $\lambda_3$ (870 mn±20 nm) may be replaced with each other.

* * * * *